US00RE37384B1

(19) United States
(12) Reissued Patent
Winter et al.

(10) Patent Number: US RE37,384 E
(45) Date of Reissued Patent: Sep. 18, 2001

(54) 2-SUBSTITUTED DISINDENYLMETALLOCENES, PROCESS FOR THEIR PREPARATION, AND THEIR USE AS CATALYSTS IN THE POLYMERIZATION OF OLEFINS

(75) Inventors: Andreas Winter, Glashütten; Martin Antberg, Hofheim am Taunus; Walter Spaleck; Jürgen Rohrmann, both of Liederbach; Volker Dolle, Kelkheim, all of (DE)

(73) Assignee: Targor GmbH (DE)

(21) Appl. No.: 09/352,824

(22) Filed: Jul. 13, 1999

Related U.S. Patent Documents

Reissue of:
(64) Patent No.: 5,145,819
Issued: Sep. 8, 1992
Appl. No.: 07/790,234
Filed: Nov. 8, 1991

(30) Foreign Application Priority Data

Dec. 11, 1990 (DE) ..... 40 35 883

(51) Int. Cl.[7] ..... C08F 4/64
(52) U.S. Cl. ..... 502/117; 502/103; 526/160; 556/7; 556/8; 556/11; 556/14; 556/19; 556/20; 556/21; 556/22; 556/43; 556/53; 556/58
(58) Field of Search ..... 502/103, 117; 556/7, 8, 11, 14, 19, 20, 21, 22, 43, 53, 58

(56) References Cited

U.S. PATENT DOCUMENTS

| | | | | |
|---|---|---|---|---|
| 4,769,510 | * | 9/1988 | Kaminsky et al. | 585/512 |
| 4,794,096 | * | 12/1988 | Ewen | 502/117 |
| 4,841,004 | * | 6/1989 | Kaminsky et al. | 556/53 |
| 4,892,851 | * | 1/1990 | Ewen | 556/43 |
| 4,933,403 | * | 6/1990 | Kaminsky et al. | 502/117 |
| 4,975,403 | * | 12/1990 | Ewen | 502/117 |
| 4,985,576 | * | 1/1991 | Roarmann et al. | 556/11 |
| 5,004,820 | * | 4/1991 | Buchwald et al. | 556/53 |
| 5,017,714 | * | 5/1991 | Welborn | 502/117 |
| 5,036,034 | * | 7/1991 | Ewen | 502/117 |
| 5,714,426 | | 2/1998 | Tsutsui et al. | 502/117 |

FOREIGN PATENT DOCUMENTS

| | | | |
|---|---|---|---|
| 0185918 | * | 6/1989 | (EP) . |
| 0344887 | * | 6/1989 | (EP) . |

OTHER PUBLICATIONS

Ewen, "Transition Metals and Organometallics as Catalyst for Olefin Polymerization" (1988) (Kaminsky and Sinn Eds) Springer–Verlag, pp. 280–289 no month available.
Mise, et al., (1989) Chem Letters, pp. 1853–1856.

* cited by examiner

*Primary Examiner*—Elizabeth D. Wood
(74) *Attorney, Agent, or Firm*—Connolly, Bove, Lodge & Hutz, LLP

(57) ABSTRACT

The novel metallocenes of the formula I (I)

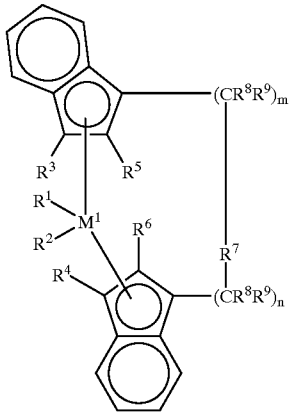

in which, preferably, $M^1$ is Zr or Hf, $R^1$ and $R^2$ are alkyl or halogen, $R^3$ and $R^4$ are hydrogen, $R^5$ and $R^6$ are alkyl or haloalkyl, $—(CR^8R^9)_m—R^7—(CR^8R^9)_n—$ is a single- or multi-membered chain in which $R^7$ may also be a (substituted) hetero atom, and m+n is zero or 1, form, together with aluminoxanes as cocatalysts, a very effective catalyst system for the preparation of polyolefins of high molecular weight.

25 Claims, No Drawings

2-SUBSTITUTED DISINDENYLMETALLOCENES, PROCESS FOR THEIR PREPARATION, AND THEIR USE AS CATALYSTS IN THE POLYMERIZATION OF OLEFINS

Matter enclosed in heavy brackets [ ] appears in the original patent but forms no part of this reissue specification; matter printed in italics indicates the additions made by reissue.

The present invention relates to novel 2-substituted bisindenylmetallocenes which can very advantageously be used as catalysts in the preparation of polyolefins of high molecular weight.

Polyolefins of high molecular weight are particularly important for the production of films, sheets or large hollow elements, such as, for example, tubes or moldings.

Chiral metallocenes are, in combination with aluminoxanes, active, stereospecific catalysts for the preparation of polyolefins (U.S. Pat. No. 4,769,510). These metallocenes also include substituted indene compounds. Thus, for example, the use of the ethylenebis(4,5,6,7-tetrahydro-1-indenyl)zirconium dichloride/aluminoxane catalyst system is known for the preparation of isotactic polypropylene (cf. EP-A 185 918). Both this and numerous other polymerization processes coming under the prior art have, in particular, the disadvantage that, at industrially interesting polymerization temperatures, only polymers having an unacceptably low molecular weight are obtained.

Surprisingly, it has now been found that novel 2-substituted bisindenylmetallocenes are suitable catalysts for the preparation of olefin polymers of high isotacticity, narrow molecular weight distribution and high molecular weight.

The present invention therefore provides the compounds of the formula I below (I)

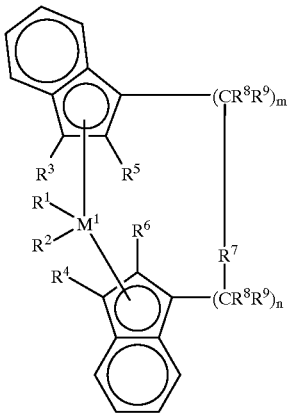

in which $M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom, $R^3$ and $R^4$ are identical or different and are a hydrogen atom, a halogen atom, a $C_1$–$C_{10}$-alkyl group, which may be halogenated, a $C_6$–$C_{10}$-aryl group, an —$NR_2^{10}$, —$SR^{10}$, —$OSiR_3^{10}$, —$SiR_3^{10}$ or —$PR_2^{10}$ radical in which $R^{10}$ is a halogen atom, a $C_1$–$C_{10}$-alkyl group or a $C_6$–$C_{10}$-aryl group, $R^5$ and $R^6$ are identical or different and are as defined for $R^3$ and $R^4$, with the proviso that $R^5$ and $R^6$ are not hydrogen,

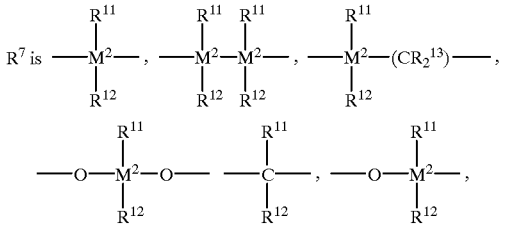

$=BR^{11}$, $=AlR^{11}$, —Ge—, —Sn—, —O—, —S—, =SO, $=SO_2$, $=NR^{11}$, =CO, $=PR^{11}$ or $=P(O)R^{11}$, where $R^{11}$, $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{11}$ and $R^{12}$ or $R^{11}$ and $R^{13}$, in each case with the atoms connecting them, form a ring, $M^2$ is silicon, germanium or tin, $R^8$ and $R^9$ are identical or different and are as defined for $R^{11}$, and m and n are identical or different and are zero, 1 or 2, m plus n being zero, 1 or 2.

Alkyl is straight-chain or branched alkyl. Halogen (halogenated) is fluorine, chlorine, bromine or iodine, preferably fluorine or chlorine.

In the formula I, $M^1$ is a metal from group IVb, Vb or VIb of the Periodic Table, for example titanium, zirconium, hafnium, vanadium, niobium, tantalum, chromium, molybdenum or tungsten, preferably zirconium, hafnium or titanium.

$R^1$ and $R^2$ are identical or different and are a hydrogen atom, a $C_1$–$C_{10}$-, preferably $C_1$–$C_3$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$- , preferably $C_7$–$C_{12}$-alkylaryl group, a $C_8$–$C_{40}$-, preferably $C_8$–$C_{12}$-aryl alkenyl group or a halogen atom, preferably chlorine.

$R^3$ and $R^4$ are identical or different and are a hydrogen atom, a halogen atom, preferably a fluorine, chlorine or bromine atom, a $C_1$–$C_{10}$-, preferably $C_1$–$C_4$-alkyl group, which may be halogenated, a $C_6$–$C_{10}$-, preferably $C_6$–$C_8$-aryl group, an —$NR_2^{10}$, —$SR^{10}$, —$OSiR_3^{10}$, —$SiR_3^{10}$, or $PR_2^{10}$ radical in whcih $R^{10}$ is a halogen atom, preferably a chlorine atom, or a $C_1$–$C_{10}$-, preferably $C_1$–$C_3$-alkyl group or a $C_6$–$C_{10}$-, preferably $C_6$–$C_8$-aryl group. $R^3$ and $R^4$ are particularly preferably hydrogen.

$R^5$ and $R^6$ are identical or different, preferably identical, and are as defined for $R^3$ and $R^4$, with the proviso that $R^5$ and $R^6$ cannot be hydrogen. $R^5$ and $R^6$ are preferably ($C_1$–$C_4$)-alkyl, which may be halogenated, such as methyl, ethyl, propyl, isopropyl, butyl, isobutyl or trifluoromethyl, in particular methyl.

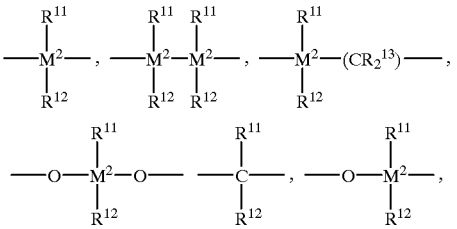

$=BR^{11}$, $=AlR^{11}$, —Ge—, —Sn—, —O—, —S—, =SO, $=SO_2$, $=NR^{11}$, =CO, $=Pr^{11}$ or $=P(O)R^{11}$, where $R^{11}$, $R^{12}$ and $R^{13}$ are identical or different and are a hydrogen atom, a halogen atom, a $C_1$–$C_{10}$-, preferably $C_1$–$C_4$-alkyl group, in particular a methyl group, a $C_1$–$C_{10}$-fluoroalkyl group, preferably a $CF_3$ group, a $C_6$–$C_{10}$-, preferably $C_6$–$C_8$-aryl group, a $C_6$–$C_{10}$-fluoroaryl group, preferably a pentafluorophenyl group, a $C_1$–$C_{10}$-, preferably $C_1$–$C_4$-alkoxy group, in particular a methoxy group, a $C_2$–$C_{10}$-, preferably $C_2$–$C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group or a $C_7$–$C_{40}$-, preferably $C_7$–$C_{12}$-alkylaryl group, or $R^{11}$ and $R^{12}$ or $R^{11}$ and $R^{13}$, in each case together with the atoms connecting them, form a ring.

$M^2$ is silicon, germanium or tin, preferably silicon or germanium.

$R^7$ is preferably $=CR^{11}R^{12}$, $=SiR^{11}R^{12}$, $=GeR^{11}R^{12}$, —O—, —S—, =SO, $=PR^{11}$ or $=P(O)R^{11}$.

$R^8$ and $R^9$ are identical or different and are as defined as for $R^{11}$.

m and n are identical or different and are zero, 1 or 2, preferably zero or 1, where m plus n is zero, 1 or 2, preferably zero or 1.

The particularly preferred metallocenes are thus those in which, in the formula I, $M^1$ is Zr or Hf, $R^1$ and $R^2$ are identical or different and are methyl or chlorine, $R^3$ and $R^4$ are hydrogen, $R^5$ and $R^6$ are identical or different and are methyl, ethyl or trifluoromethyl, $R^7$ is a

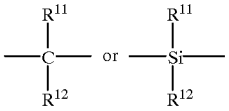

radical, and n plus m is zero or 1; in particular the compounds I listed in the working examples.

Of the compounds I mentioned in the working examples, rac-dimethylsilyl(2-methyl-1-indenyl)$_2$zirconium dichloride, rac-ethylene(2-methyl-1-indenyl)$_2$zirconium dichloride, rac-dimethylsilyl(2-methyl-1-indenyl)$_2$dimethylzirconium and rac-ethylene(2-methyl-1-indenyl)$_2$dimethylzirconium are particularly important.

The chiral metallocenes are employed as racemates for the preparation of highly isotactic poly-1-olefins. However, it is also possible to use the pure R- or S-form. These pure stereoisomeric forms allow the preparation of an optically active polymer. However, the meso form of the metallocenes should be separated off since the polymerization-active center (the metal atom) in these compounds is no longer chiral due to mirror symmetry at the central metal, and it is therefore not possible to produce a highly isotactic polymer. If the meso form is not separated off, atactic polymer is formed alongside isotactic polymers. For certain applications—soft moldings for example—this may be entirely desirable.

The principle of resolution of the stereoisomers is known.

The present invention furthermore provides a process for the preparation of the metallocenes I, which comprises reacting a compound of the formula II

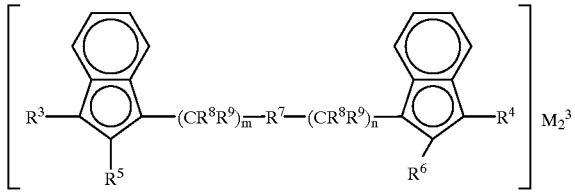

(II)

where $R^3$–$R^9$, m and n are as described in the formula I, and $M^3$ is an alkali metal, preferably lithium, a) with a compound of the formula III $$M^1X_4 \quad \text{(III)}$$

in which $M^1$ is as defined in the formula I, and X is a halogen atom, preferably chlorine, or b) with a compound of the formula IIIa $$M^1X_4L_2 \quad \text{(IIIa)}$$

in which $M^1$ and X are as defined above, and L is a donor ligand, and, if desired, derivatizing the resultant reaction product.

Examples of suitable donor ligands are tetrahydrofuran, diethyl ether, dimethyl ether and the like, preferably tetrahydrofuran (THF).

The synthesis is carried out under a protective gas and in anhydrous solvents. In case a), the dried salt of the formula II is added to a suspension of the compound of the formula III in a solvent such as toluene, n-hexane, dichloromethane, ether, THF, n-pentane or benzene, preferably in dichloromethane or toluene. The reaction temperature is from −78° C. to 30° C., preferably from −40° C to 10° C. The reaction duration is from 0.25 to 24 hours, preferably from 1 to 4 hours.

In case b), a solution of the salt of the formula II in one of the abovementioned solvents is added to a solution or suspension of a compound of the formula IIIa in a solvent such as toluene, xylene, ether or THF, preferably THF. However, an alternative procedure is to simultaneously add both components dropwise to a solvent. This is the preferred procedure. The reaction temperature is from −40° C. to 100° C., preferably from 0° C. to 50° C., in particular from 10° C. to 35° C. The reaction duration is from 0.25 hour to 48 hours, preferably from 1 hour to 24 hours, in particular from 2 hours to 9 hours.

The halogen derivatives obtained in this way can be converted into the alkyl, aryl or alkenyl complexes by known standard methods.

The compounds of the formula II are synthesized by deprotonation. This reaction is known; cf. J. Am. Chem. Soc., 112 (1990) 2030–2031, ibid. 110 (1988) 6255–6256, ibid. 109 (1987), 6544–6545, J. Organomet. Chem., 322 (1987) 65–70, New. J. Chem. 14 (1990) 499–503 and the working examples.

The synthesis of the protonated forms of the compounds of these formulae has also been described, with the difference that they are not correspondingly substituted in the α- and β-positions (Bull. Soc. Chim., 1967, 2954). The bridging units required for their synthesis are generally commercially available, but the indenyl compounds required, by contrast, are not. Some literature references containing synthesis procedures are indicated; the procedure for indene derivatives which are not mentioned is analogous: J. Org. Chem., 49 (1984) 4226–4237, J. Chem. Soc., Perkin II, 1981, 403–408, J. Am. Chem. Soc., 106 (1984) 6702, J. Am. Chem. Soc., 65 (1943) 567, J. Med. Chem., 30 (1987) 1303–1308, Chem. Ber. 85 (1952) 78–85 and the working examples.

The metallocenes I can thus in principle be prepared in accordance with the reaction scheme below:

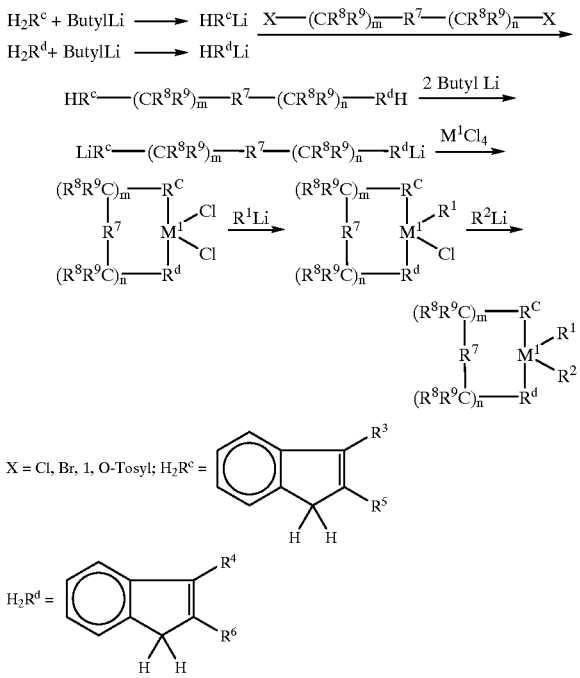

The cocatalyst used according to the invention in the polymerization of olefins is an aluminoxane of the formula (IV)

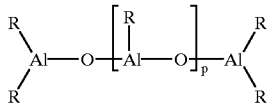

(IV)

for the linear type and/or of the formula (V)

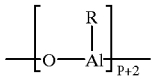

(V)

for the cyclic type, where, in the formulae (IV) and (V), the radicals R may be identical or different and are a $C_1$–$C_6$-alkyl group, a $C_6$–$C_{18}$-aryl group or hydrogen, and p is an integer from 2 to 50, preferably from 10 to 35.

The radicals R are preferably identical and are methyl, isobutyl, phenyl or benzyl, particularly preferably methyl.

If the radicals R are different, they are preferably methyl and hydrogen or alternatively methyl and isobutyl, from 0.01 to 40% (of the number of radicals R) being hydrogen or isobutyl.

The aluminoxane can be prepared in different ways by known processes. One of the methods is, for example, the reaction of an aluminum-hydrocarbon compound and/or a hydridoaluminum-hydrocarbon compound with water (gaseous, solid, liquid or bound—for example as water of crystallization) in an inert solvent (such as, for example, toluene). In order to prepare an aluminoxane containing different alkyl groups R, two different trialkylaluminum compounds ($AlR_3$+$AlR'_3$) in accordance with the desired composition are reacted with water (cf. S. Pasynkiewicz, Polyhedron 9 (1990) 429 and EP-A 302 424).

The precise structure of the aluminoxanes IV and V is not known.

Irrespective of the preparation method, a varying content of unreacted aluminum starting compound, in free form or as an adduct, is common to all the aluminoxane solutions.

It is possible to preactivate the metallocene I using an aluminoxane of the formula (IV) and/or (V) before use in the polymerization reaction. This considerably increases the polymerization activity and improves the particle morphology.

The preactivation of the transition-metal compound is carried out in solution. The metallocene is preferably dissolved in a solution of the aluminoxane in an inert hydrocarbon. Suitable inert hydrocarbons are aliphatic or aromatic hydrocarbons. Toluene is preferred.

The concentration of the aluminoxane in the solution is in the range from about 1% by weight up to the saturation limit, preferably from 5 to 30% by weight, in each case based on the entire solution. The metallocene can be employed in the same concentration, but is preferably employed in an amount of from $10^{-4}$–1 mol per mole of aluminoxane. The preactivation time is from 5 minutes to 60 hours, preferably from 5 to 60 minutes. The preactivation temperature is from −78° C. to 100° C., preferably from 0° to 70° C.

The metallocene can also be prepolymerized or applied to a support. The prepolymerization is preferably carried out using the olefin or one of the olefins employed in the polymerization.

Examples of suitable supports are silica gels, aluminum oxides, solid aluminoxane or other inorganic support materials. Another suitable support material is a polyolefin powder in finely divided form.

A further possible variation of the process comprises using a salt-like compound of the formula $R_xNH_{4-x}BR'_4$ or of the formula $R_3PHBR'_4$ as cocatalyst instead of or in addition to an aluminoxane. x here is 1, 2 or 3, the R radicals are identical or different and are alkyl or aryl, and R' is aryl, which may also be fluorinated or partially fluorinated. In this case, the catalyst comprises the product of the reaction of a metallocene with one of said compounds (cf. EP-A 277 004).

The polymerization or copolymerization is carried out in a known manner in solution, in suspension or in the gas phase, continuously or batchwise, in one or more steps, at a temperature of from 0° to 150° C., preferably from 30° to 80° C. Olefins of the formula $R^a$—CH═CH—$R^b$ are polymerized or copolymerized. In this formula, $R^a$ and $R^b$ are identical or different and are a hydrogen atom or an alkyl radical having 1 to 14 carbon atoms. However, $R^a$ and $R^b$, together with the carbon atoms connecting them, may also form a ring. Examples of such olefins are ethylene, propylene, 1-butene, 1-hexene, 4-methyl-1-pentene, 1-octene, norbornene or norbornadiene. In particular, propylene and ethylene are polymerized.

The molecular weight regulator added, if necessary, is hydrogen. The overall pressure in the polymerization system is from 0.5 to 100 bar. The polymerization is preferably carried out in the industrially particularly interesting pressure range of from 5 to 64 bar.

The metallocene is used in a concentration, based on the transition metal, of from $10^{-3}$ to $10^{-8}$, preferably from $10^{-4}$ to $10^{-7}$ mol of transition metal per $dm^3$ of solvent or per $dm^3$ of reactor volume. The aluminoxane is used in a concentration of from $10^{-5}$ to $10^{-1}$ mol, preferably from $10^{-4}$ to $10^{-2}$ mol, per $dm^3$ of solvent or per $dm^3$ of reactor volume. In principle, however, higher concentrations are also possible.

If the polymerization is carried out as a suspension or solution polymerization, an inert solvent which is customary for the Ziegler low-pressure process is used. For example, the polymerization is carried out in an aliphatic or cycloaliphatic hydrocarbon; examples of these which may be mentioned are butane, pentane, hexane, heptane, isooctane, cyclohexane and methylcyclohexane.

It is also possible to use a petroleum ether or hydrogenated diesel oil fraction. Toluene can also be used. The polymerization is preferably carried out in the liquid monomer.

If inert solvents are used, the monomers are metered in in gaseous or liquid form.

The polymerization can have any desired duration since the catalyst system to be used according to the invention exhibits only a low time-dependent drop in polymerization activity.

The process is distinguished by the fact that the metallocenes according to the invention give, in the industrially interesting temperature range of between 30° and 80° C., polymers of high molecular weight, high stereospecificity and good particle morphology.

The zirconocenes according to the invention, in particular, are in a molecular weight range which was the province of the hafnocenes in the previous prior art. However, the latter had the disadvantage of only low polymerization activity and very high catalyst costs, and the polymers prepared using them had poor powder morphology.

The examples below are intended to illustrate the invention in greater detail.

SYNTHESIS OF THE STARTING SUBSTANCES

I) Synthesis of 2-Me-indene 110.45 g (0.836 mol) of 2-indanone were dissolved in 500 $cm^3$ of diethyl ether, and 290 $cm^3$ of 3 N (0.87 mol) ethereal methylGrignard solution were added dropwise at such a rate that the mixture refluxed gently. After the mixture had boiled for 2 hours under gentle reflux, it was transferred onto an ice/hydrochloric acid mixture, and a pH of 2–3 was established using ammonium chloride. The organic phase was separated off, washed with $NaHCO_3$ and sodium chloride solution and dried, giving 98 g of crude product (2-hydroxy-2-methylindane), which was not purified further.

This product was dissolved in 500 $cm^3$ of toluene, 3 g of p-toluenesulfonic acid were added, and the mixture was heated on a water separator until the elimination of water was complete, and was evaporated, the residue was taken up in dichloromethane, the dichloromethane solution was filtered through silica gel, and the filtrate was distilled in vacuo (80° C./10 mbar). Yield: 28.49 g (0.22 mol/26%).

The synthesis of this compound is also described in: C. F. Koelsch, P. R. Johnson, J. Am. Chem. Soc., 65 (1943) 567–573.

II) Synthesis of (2-Me-indene)$_2$SiMe$_2$ 13 g (100 mmol) of 2-Me-indene were dissolved in 400 $cm^3$ of diethyl ether, and 62.5 $cm^3$ of 1.6 N (100 mmol) n-butyllithium/n-hexane solution were added dropwise over the course of 1 hour with ice cooling, and the mixture was then stirred at ~35° C. for a further 1 hour.

6.1 $cm^3$ (50 mmol) of dimethyldichlorosilane were introduced into 50 $cm^3$ of $Et_2O$, and the lithio salt solution was added dropwise at 0° C. over the course of 5 hours, the mixture was stirred overnight at room temperature and left to stand over the weekend.

The solid which had deposited was filtered off, and the filtrate was evaporated to dryness. The product was extracted using small portions of n-hexane, and the extracts were filtered and evaporated, giving 5.7 g (18.00 mmol) of white crystals. The mother liquor was evaporated, and the residue was then purified by column chromatography (n-hexane/$H_2CCl_2$ 9:1 by volume), giving a further 2.5 g (7.9 mmol/52%) of product (as an isomer mixture).

$R_f$ ($SiO_2$; n-hexane/$H_2CCl_2$ 9:1 by volume)=0.37.

The $^1$H-NMR spectrum exhibits the signals expected for an isomer mixture with respect to shift and integration ratio.

III) Synthesis of (2-Me-Ind)$_2$CH$_2$CH$_2$ 3 g (23 mmol) of 2-Me-indene were dissolved in 50 $cm^3$ of THF, 14.4 $cm^3$ of 1.6 N (23.04 mmol) n-butyllithium/n-hexane solution were added dropwise, and the mixture was then stirred at 65° C. for 1 hour. 1 ml (11.5 mmol) of 1,2-dibromoethane was then added at −78° C., and the mixture was allowed to warm to room temperature and was stirred for 5 hours. The mixture was evaporated, and the residue was purified by column chromatography ($SiO_2$; n-hexane/$H_2CCl_2$ 9:1 by volume).

The fractions containing the product were combined and evaporated, the residue was taken up in dry ether, the solution was dried over $MgSO_4$ and filtered, and the solvent was stripped off.

Yield: 1.6 g (5.59 mmol/49%) of isomer mixture $R_f$ ($SiO_2$; n-hexane/$H_2CCl_2$ 9:1 by volume) =0.46.

The $^1$H-NMR spectrum corresponds to expectations for an isomer mixture in signal shift and integration.

SYNTHESIS OF THE METALLOCENES I

IV) Synthesis of rac-dimethylsilyl(2-Me-1-indenyl)$_2$-zirconium dichloride 1.68 g (5.31 mmol) of the chelate ligand dimethylsilyl (2-methylindene) were introduced into 50 $cm^3$ of THF, and 6.63 $cm^3$ of a 1.6 N (10.61 mmol) n-BuLi/n-hexane solution were added dropwise at ambient temperature over the course of 0.5 hour. The mixture was stirred for 2 hours at about 35° C., the solvent was stripped off in vacuo, and the residue was stirred with n-pentane, filtered off and dried.

The dilithio salt obtained in this way was added at −78° C. to a suspension of 1.24 g (5.32 mmol) of $ZrCl^4$ in 50 $cm^3$ of $CH_2Cl_2$, and the mixture was stirred at this temperature for 3 hours. The mixture was then warmed to room temperature overnight and evaporated. The $^1$H-NMR spectrum showed, in addition to the presence of some $ZrCl_4(thf)_2$, a rac/meso mixture. After stirring with n-pentane and drying, the solid, yellow residue was suspended in THF, filtered off and examined by NMR spectroscopy. These three working steps were repeated a number of times; finally, 0.35 g (0.73 mmol/14%) of product was obtained in which the rac form, according to $^1$H-NMR, was enriched to more than 17:1.

The compound exhibited a correct elemental analysis and the following NMR signals ($CDCl_3$, 100 MHz): δ=1.25 (s, 6H, Si-Me); 2.18 (s, 6H, 2-Me); 6.8 (s, 2H, 3-H-Ind); 6.92–7.75 (m, 8H, 4-7-H-Ind).

V) rac-Dimethylsilyl-(2-Me-l-indenyl)$_2$dimethyl zirconium 0.24 g (0.58 mmol) of rac-dimethylsilyl(2-Me-1-indenyl)$_2$zirconium dichloride in 40 $cm^3$ of $Et_2O$ was added dropwise at −50° C. with 1.3 $cm^3$ of a 1.6 N (2.08 mmol) ethereal MeLi solution, and the mixture was stirred at −10° C. for 2 hours. The solvent was replaced by n-pentane, the mixture was stirred at room temperature for a further 1.5 hours, and the filtered residue was sublimed in vacuo, giving 0.19 g (0.44 mmol/81%) of sublimate having a correct elemental analysis.

VI) rac-Ethylene(2-Me-1-indenyl)$_2$zirconium dichloride 14.2 $cm^3$ of 2.5 N (35.4 mmol) n-BuLi/n-hexane solution were added dropwise over the course of 1 hour at room temperature to 5.07 g (17.7 mmol) of the ligand ethylene (2-methylindene)$_2$ in 200 $cm^3$ of THF, and the mixture was then stirred at about 50° C. for 3 hours. A precipitate which formed temporarily dissolved again. The mixture was left to stand overnight.

6.68 g (17.7 mmol) of $ZrCl_4(thf)_2$ in 250 $cm^3$ of THF were added dropwise, simultaneously with the above dilithio salt solution, to about 50 $cm^3$ of THF at 50° C., and the mixture was then stirred at this temperature for 20 hours. The toluene extract of the evaporation residue was evaporated. The residue was extracted with a little THF, and the product was recrystallized from toluene, giving 0.44 g (0.99 mmol/5.6%) of product in which the rac form was enriched to more than 15:1.

The compound exhibited a correct elemental analysis and the following NMR signals ($CDCl_3$, 100 MHz): δ=2.08 (2s, 6H, 2-Me); 3.45–4.18 (m, 4H, —$CH_2CH_2$—) ; 6.65 (2H, 3-H-Ind); 7.05–7.85 (m, 8H, 4-7-H-Ind).

VII) $Me_2Zr[(2\text{-Me-Ind})_2CH_2CH_2]$ 1.43 g (3.20 mmol) of $Cl_2Zr[(2\text{-Me-Ind})_2CH_2CH_2]$ were dissolved in 50 $cm^3$ of $Et_2O$, and 6 $cm^3$ of 1.6 N (9.6 mmol) ethereal methyllithium solution were added dropwise at −40° C. The mixture was stirred at −10° C. for 2 hours and evaporated, the residue was taken up in n-hexane, the solution was stirred at room temperature for 1 hour, filtered and evaporated, and the product was sublimed.

Yield: 1.20 g (2.96 mmol/92%); correct elemental analysis.

VIII) $Cl_2Zr[(2\text{-Me-Ind})_2SiPh_2]$ 12.5 $cm^3$ of 1.6 N (20 mmol) n-butyllithium/n-hexane solution were added dropwise over the course of 0.5 hour at room temperature to 4.41 g (10 mmol) of $(2\text{-Me-Ind})_2SiPh_2$ in 40 $cm^3$ of THF, and the mixture was then stirred at 55° C. for 1 hour. The solvent was stripped off, and the residue was stirred in n-hexane, filtered off and dried in vacuo.

2.33 g (10 mmol) of $ZrCl_4$ were suspended in 50 $cm^3$ of $H_2CCl_2$, the dilithio salt from the above reaction was added at −78° C., and the mixture was warmed to room temperature overnight. The mixture was filtered and evaporated, and the residue was washed with several small portions of THF and then dried in vacuo, giving 2.11 g (3.51 mmol/35%) of product. The elemental analysis corresponded to the C, H, Cl values required.

IX) $Cl_2Zr[(2\text{-Me-Ind})_2SiMePh]$

12 $cm^3$ of 2.5 N (30 mmol) n-butyllithium/n-hexane solution were added dropwise over the course of 1 hour at 10° C. to 5.68 g (15 mmol) of $(2\text{-Me-Ind})_2SiMePh$ in 50 $cm^3$ of THF, and the mixture was then stirred at 50° C. for 1 hour and evaporated. The residue was suspended in n-hexane, filtered off and dried in vacuo.

3.5 g (15.02 mmol) of $ZrCl_4$ were suspended in 100 $cm^3$ of $H_2CCl_2$, and the dilithio salt was added at −78° C. The mixture was then stirred at −25° C. for 6 hours and at 0° C. for 2 hours and then filtered. The filtrate was evaporated, and the residue was extracted a number of times with a little THF and then dried in vacuo.

Yield: 1.47 g (2.73 mmol/18%); with correct elemental analysis.

X) $Cl_2Zr[(2\text{-Et-Ind})_2CH_2CH_2]$ 9.6 $cm^3$ of 2.5 N (24 mmol) n-butyllithium/n-hexane solution were added dropwise over the course of 10 minutes at room temperature to 3.77 g (11.99 mmol) of $(2\text{-Et-Ind})_2CH_2CH_2$ in 150 $cm^3$ of THF. The mixture was stirred at 50° C. for 2 hours, and the resultant dilithio salt solution was cooled to ambient temperature and added dropwise over the course of 6 hours at 35° C., simultaneously with an equal-volume solution of 4.53 g (12 mmol) of $ZrCl_4$, to 50 $cm^3$ of THF, and stirring was continued overnight. The evaporated batch was extracted with several portions of a toluene/n-hexane mixture (3:1 by volume), and the extracts were filtered and evaporated. The residue was washed with small portions of THF and dried in vacuo.

Yield: 2.37 g (4.99 mmol/42%). The elemental analysis was correct.

XI) $Cl_2Zr[(2\text{-Et-Ind})_2SiMe_2]$ 22 5 $cm^3$ of 1.6 N (36 mmol) ethereal methyllithium solution were added dropwise over the course of 1 hour at room temperature to 6.2 g (18 mmol) of $(2\text{-Et-Ind})_2SiMe_2$ in 150 $cm^3$ of THF, and the mixture was stirred at 45° C. until the evolution of gas was complete. The solvent was stripped off, and the residue was then digested in n-pentane, filtered off and dried in vacuo.

The dilithio salt was added at −45° C. to 4.2 g (18.02 mmol) of $ZrCl_4$ suspended in 100 $cm^3$ of $H_2CCl_2$, and the mixture was allowed to warm to −20° C. The mixture was stirred at this temperature for 3 hours, warmed to room temperature, filtered and evaporated. The residue was then extracted with several portions of toluene, and the extracts were filtered and evaporated. The residue was stirred with n-hexane, filtered off and dried in vacuo.

Yield: 1.04 g (2.06 mmol/11%). The substance exhibited a correct elemental analysis.

XII) $Cl_2Zr[(2\text{-Me-Ind})_2CHMeCH_2]$ 8.85 $cm^3$ of 1.6 N (14.16 mmol) n-butyllithium/n-hexane solution were added dropwise over the course of 0.5 hour at room temperature to 2.12 g (7.06 mmol) of $(2\text{-Me-Ind})_2CHMeCH_2$ in 40 $cm^3$ of THF, and the mixture was then stirred at 55° C. for 1.5 hours. This solution was then added at 0° C. over a period of 2 hours to 2.66 g (7.05 mmol) of $ZrCl_4(thf)_2$ in 50 $cm^3$ of THF. The mixture was stirred at room temperature for 2 hours and evaporated, the residue was extracted with several small portions of toluene/n-hexane 1:1 (by volume), the extracts were evaporated, the residue was extracted with warm n-hexane, the extracts were evaporated, and the residue was filtered off.

Yield: 0.44 g (0.96 mmol/14%); correct elemental analysis.

XIII) $Cl_2Zr[(2\text{-Me-Ind})_2CMe_2]$ 8.2 $cm^3$ (13.12 mmol) of 1.6 N ethereal methyllithium solution were added dropwise at 0° C. to 1.97 g (6.56 mmol) of $(2\text{-Me-Ind})_2CMe_2$dissolved in 60 $cm^3$ of $Et_2O$, and the mixture was then refluxed for 2 hours and evaporated. The residue was stirred with n-hexane, separated off and dried in vacuo.

The dilithio salt obtained was added at −50° C. to a suspension of 1.53 g (6.57 mmol) of $ZrCl_4$ in 60 $cm^3$ of $H_2CCl_2$, the mixture was stirred at −35° C. for 3 hours, warmed to room temperature and filtered, the residue was extracted with a few portions of toluene/n-hexane, the extracts were evaporated, the residue was stirred with n-pentane, and the solvent was stripped off in vacuo.

Yield: 0.81 g (1.76 mmol/27%); correct elemental analysis.

XIV) $Me_2Zr[(2\text{-Me-Ind})_2SiMePh]$ 6.5 $cm^3$ of 1.6 N (10.4 mmol) ethereal methyllithium solution were added dropwise at −50° C. to 2.29 g (4.25 mmol) of $Cl_2Zr[(2\text{-Me-Ind})_2SiMePh]$ dissolved in 50 $cm^3$ of $Et_2O$, and the mixture was stirred at −25° C. for 2.5 hours. The solvent was replaced by n-hexane, and the mixture was stirred at room temperature for a further 1 hour and filtered, the filtrate was concentrated somewhat and re-filtered, and the solvent was evaporated.

Yield: 1.58 g (3.17 mmol/75%); correct elemental analysis.

Abbreviations:

Me=methyl, Et=ethyl, Bu=butyl, Ph=phenyl, Ind=indenyl, THF=tetrahydrofuran, PP=polypropylene, PE=polyethylene.

METALLOCENES I AS CATALYSTS FOR THE POLYMERIZATION OF OLEFINS

The following abbreviations are used:

| | |
|---|---|
| VN = viscosity number in $cm^3/g$<br>$M_w$ = weight average molecular weight in g/mol<br>$M_w/M_n$ = molecular weight dispersity | determined by gel permeation chromatography |
| II = isotactic index (II = mm + ½ r), determined by $^{13}C$-NMR spectroscopy<br>BD = polymer bulk density in $g/dm^3$<br>MFI (230/5) = melt flow index in g/10 min, measured in accordance with DIN 53735 | |

EXAMPLE 1

12 $dm^3$ of liquid propylene were introduced into a dry 24 $dm^3$ reactor which had been flushed with nitrogen.

35 $cm^3$ of a toluene solution of methylaluminoxane (corresponding to 52 mmol of Al, mean degree of oligomerization n=17) were then added, and the batch was stirred at 30° C. for 15 minutes.

In parallel, 6.9 mg (0.015 mmol) of rac-ethylene -(2-Me-1-Indenyl)zzirconium dichloride were dissolved in 13.5 $cm^3$ of a toluene solution of methylaluminoxane (20 mmol of Al) and preactivated by standing for 15 minutes.

The solution was then introduced into the reactor and heated to 70° C. (10° C./min) by supply of heat, and the polymerization system was kept at 70° C for 1 hour by cooling. The polymerization was terminated by removing the excess monomer in gas form. 1.56 kg of polypropylene were obtained.

The activity of the metallocene was thus 226 kg of PP/g of metallocene×h.

VN=67 $cm^3/g$; $M_w$=58 900 g/mol; $M_w/M_n$=2.0; II=95.9%;

BD=350 $g/dm^3$.

EXAMPLE 2

Example 1 was repeated, but 10.1 mg (0.023 mmol) of the metallocene were used and the polymerization was carried out at 50° C.

0.51 kg of polymer powder were obtained, corresponding to a metallocene activity of 50.5 kg of PP/g of metallocene× h.

VN=100 $cm^3/g$; $M_w$=108 500 g/mol; $M_w/M_n$=2.2; II=96.4%; MFI (230/5)=210 g/10 min.

EXAMPLE 3

Example 1 was repeated, but 10.5 mg (0.023 mmol) of the metallocene were employed and the polymerization was carried out at 30° C. for 10 hours.

1.05 kg of polymer powder were obtained, corresponding to a metallocene activity of 10.0 kg of PP/g of metallone ×h.

VN=124 $cm^3/g$; $M_w$=157 000 g/mol; $M_w/M_n$=2.2; II=96.3%; MFI (230/5)=104 g/10 min.

COMPARATIVE EXAMPLES A–C

The polymerization was carried out in an analogous manner to Examples 1 to 3 using the metallocene rac-ethylenebisindenylzirconium dichloride. The viscosity numbers and molecular weights of the resultant polymer products were:

| Comp. Ex. | Polym. temp. [° C.] | VN [$cm^3/g$] | $M_w$ [g/mol] |
|---|---|---|---|
| A | 70 | 30 | 19 900 |
| B | 50 | 46 | 38 500 |
| C | 30 | 60 | 48 700 |

These comparative examples demonstrate the molecular weight-increasing effect of the substituent in the 2-position on the indenyl ligand.

EXAMPLE 4

The procedure was as in Example 1, but 4.0 mg (0.008 mmol) of rac-dimethylsilyl(2-methyl-1-indenyl)$_2$-zirconium dichloride were used.

The metallocene activity was 293 kg of PP/g of metallocene ×h.

VN=171 $cm^3/g$; $M_w$=197 000 g/mol; $M_w/M_n$=2.5; II=96.0%; MFI (230/5)=43.2 g/10 min; BD=460 $g/dm^3$; m.p.=145° C.

EXAMPLE 5

The procedure was as in Example 1, but 6.0 mg (0.013 mmol) of rac-dimethylsilyl(2-methyl-1-indenyl)$_2$-zirconium dichloride were used.

The polymerization temperature was 60° C. and the polymerization time was 1 hour.

The metallocene activity was 178 kg of PP/g of metallocene ×h.

VN=217 $cm^3/g$; $M_w$=297 000 g/mol; $M_w/M_n$=2.3; II=96.4%; MFI (230/5)=12.9 g/10 min; m.p.=148° C.

EXAMPLE 6

The procedure was as in Example 1, but 2.4 mg (0.0052 mmol) of rac-dimethylsilyl(2-methyl-1-indenyl)$_2$-zirconium dichloride were used. The polymerization temperature was 50° C. and the polymerization time was 3 hours.

The metallocene activity was 89 kg of PP/g of metallocene ×h.

VN=259 $cm^3/g$; $M_w$=342 500 g/mol; $M_w/M_n$=2.1; II=96.8%; MFI (230/5)=8.1 g/10 min; m.p.=150° C.

EXAMPLE 7

The procedure was as in Example 1, but 9.9 mg (0.021 mmol) of rac-dimethylsilyl(2-methyl -1-indenyl)$_2$-zirconium dichloride were used.

The polymerization temperature was 30° C. and the polymerization time was 2 hours.

The metallocene activity was 26.5 kg of PP/g of metallocene ×h.

VN=340 $cm^3/g$; $M_w$=457 000 g/mol; $M_w/M_n$=2.4; II=96.0%; MFI (230/5)=2.5 g/10 min.

EXAMPLE 8

6 $dm^3$ of a gasoline fraction having a boiling range of 100°–120° C. with the aromatic components removed, and 6 $dm^3$ of liquid propylene were introduced into a dry 24 $dm^3$ reactor which had been flushed with nitrogen. 35 $cm^3$ of a toluene solution of methylaluminoxane (corresponding to 52 mmol of Al, mean degree of oligomerization n=17) were then added, and the batch was stirred at 30° C. for 30 minutes.

In parallel, 14.7 mg (0.031 mmol) of rac-dimethylsilyl (2-methyl-1-indenyl)zzirconium dichloride were dissolved in 13.5 $cm^3$ of a toluene solution of methylaluminoxane (20 mmol of Al) and preactivated by standing for 30 minutes.

The solution was then introduced into the reactor, the polymerization system was kept at 50° C. for 1 hour by cooling. The polymerization was terminated by addition of 50 $cm^3$ of isopropanol.

The metallocene activity was 159.2 kg of PP/g of metallocene ×h.

VN=188 $cm^3/g$; $M_w$=240 000 g/mol; $M_w/M_n$=2.1; II=96.0%; MFI (230/5)=28.6 g/10 min.

EXAMPLE 9

Example 8 was repeated, but 15.2 mg (0.032 mmol) of the metallocene were used, the polymerization time was 2 hours, and the polymerization temperature was 30° C.

The metallocene activity was 24.1 kg of PP/g of metallocene ×h.

VN=309 $cm^3/g$; $M_w$=409 000 g/mol; $M_w/M_n$=2.3; II=97.0%; MFI (230/5)=3.5 g/10 min.

COMPARATIVE EXAMPLES D–F

The polymerization was carried out in an analogous manner to Examples 4, 6 and 7 using the metallocene dimethylsilylbisindenylzirconium dichloride. The viscosity numbers and molecular weights of the resultant polymer products were:

| Comp. Ex. | Polym. temp. [° C.] | VN [$cm^3/g$] | $M_w$ [g/mol] |
|---|---|---|---|
| D | 70 | 47 | 37 500 |
| E | 50 | 60 | 56 000 |
| F | 30 | 77 | 76 900 |

These examples demonstrate the molecular weight-increasing effect of the substituent in the 2-position on the indenyl ligand.

EXAMPLE 10

Example 1 was repeated, but 4.1 mg (0.008 mmol) of the metallocene rac-phenyl(methyl)silyl(2-methyl-1-indenyl)$_2$-$ZrCl_2$ were used.

1.10 kg of polypropylene were obtained, corresponding to a metallocene activity of 269 kg of PP/g of metallocene ×h.

VN=202 $cm^3/g$; $M_w$=230 000 g/mol; $M_w/M_n$=2.3; II=97%; MFI (230/5)=36 g/10 min; m.p.=147° C.

EXAMPLE 11

Example 1 was repeated, but 5.2 mg (0.009 mmol) of the metallocene rac-diphenylsilyl(2-methyl-1-indenyl)$_2$$ZrCl_2$ were used.

1.14 kg of polypropylene were obtained. The metallocene activity was thus 219 kg of PP/g of metallocene×h.

VN=298 $cm^3$g; $M_w$=367 000 g/mol; $M_wM_n$=2.2; MFI (230/5)=7.1 g/10 min.

EXAMPLE 12

Example 1 was repeated, but 17.4 mg (0.038 mmol) of the metallocene rac-methylethylene(2-methyl-1-indenyl)$_2$$ZrCl_2$ were used.

2.89 kg of polypropylene were obtained. The metallocene activity was thus 165.9 kg of PP/g of metallocene×h.

VN=138 $cm^3/g$; $M_w$=129 000 g/mol; $M_w/M_n$=2.2; m.p.= 150° C.

EXAMPLE 13

Example 1 was repeated, but 9.6 mg (0.02 mmol) of the metallocene rac-dimethylsilyl(2-ethyl-1-indenyl)$_2$-zirconium dichloride were used.

1.68 kg of polypropylene, corresponding to a metallocene activity of 175.0 kg of PP/g of metallocene×h, were obtained.

VN=143 $cm^3/g$; $M_w$=132 000 g/mol; $M_w/M_n$=2.3; m.p.= 140° C.

We claim:

1. A compound of the formula I (I)

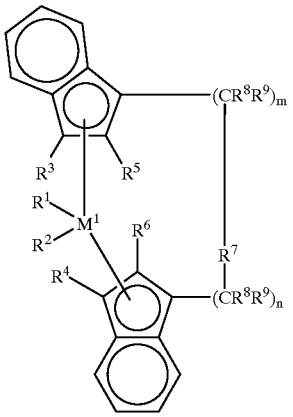

in which $M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom, $R^3$ and $R^4$ are identical or different and are a hydrogen atom, a halogen atom, a $C_1$–$C_{10}$-alkyl group, which is optionally halogenated, a $C_6$–$C_{10}$-aryl group, an $—NR_2^{10}$, $—SR^{10}$, $—OSiR_2^{10}$. $—SiR_3^{10}$ or $—PR_2^{10}$ radical in which $R^{10}$ is a halogen atom, a $C_1$–$C_{10}$-alkyl group or a $C_6$–$C_{10}$-aryl group, $R^5$ and $R^6$ are identical or different and are as defined for $R^3$ and $R^4$, with the proviso that $R^5$ and $R^6$ are not hydrogen, $R^7$ is

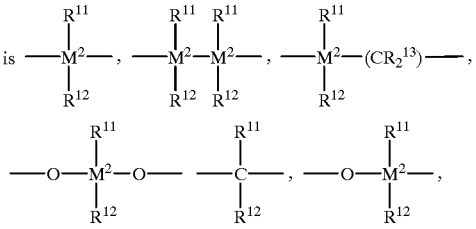

$=Br^{11}$, $=AlR^{11}$, —Ge—, —Sn—, —O—, —S—, =SO, $=SO_2$, $=NR^{11}$, =CO, $=PR^{11}$ or $=P(O)R^{11}$, where $R^{11}$, $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{11}$ and $R^{12}$ or $R^{11}$ and $R^{13}$, in each case with the atoms connecting them, form a ring, $M^2$ is silicon, germanium or tin, $R^8$ and $R^9$ are identical or different and are as defined for $R^{11}$, and m and n are identical or different and are zero[, 1 or 2, m plus n being zero, 1 or 2].

2. A compound of the formula I as claimed in claim 1, wherein, in the formula I, $M^1$ is Zr or Hf, $R^1$ and $R^2$ are identical or different and are methyl or chlorine, $R^3$ and $R^4$ are hydrogen, $R^5$ and $R^6$ are identical or different and are methyl, ethyl or trifluoromethyl, $R^7$ is a

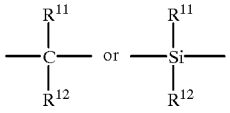

radical[, and n plus m is zero or 1].

3. A compound [of the formula I as claimed in claim 1, wherein the compound is Rac] *selected from the group consisting of rac*-dimethylsilyl(2-methyl -1-indenyl)$_2$zirconium dichloride, rac-ethylene-(2-methyl-1-indenyl)$_2$zirconium dichloride, rac-dimethylsilyl(2-methyl-1-indenyl)$_2$dimethylzirconium, rac-ethylene(2-methyl-1-indenyl)$_2$dimethylzirconium, rac-phenyl(methyl)silyl(2-methyl-1-indenyl)$_2$zirconium dichloride, rac-diphenylsilyl (2-methyl-1-indenyl)$_2$zirconium dichloride, rac-methylethylene(2-methyl-1-indenyl)$_2$zirconium dichloride, rac-dimethylsilyl (2-ethyl-1-indenyl)$_2$zirconium dichloride, rac-ethylene(2-ethyl-1-indenyl)$_2$zirconiumdichloride, rac-isopropylidene(2-methyl-1-indenyl)$_2$zirconium dichloride or rac-phenyl(methyl)silyl(2-methyl 1-indenyl)$_2$dimethyl zirconium.

4. A process for the preparation of a compound of the formula I as claimed in claim 1, which comprises reacting a compound of the formula II (II)

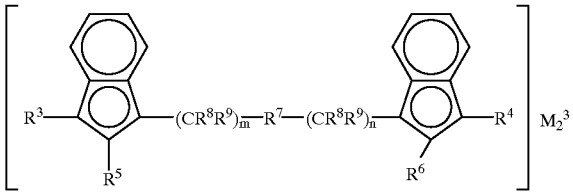

where $R^3$–$R^9$, m and n are as described in the formula I, and $M^3$ is an alkali metal, a) with a compound of the formula III $$M^1X_4 \quad \text{(III)}$$

in which $M^1$ is as defined in the formula I, and X is a halogen atom, or b) with a compound of the formula IIIa $$M^1X_4L_2 \quad \text{(IIIa)}$$

in which $M^1$ and X are as defined above, and L is a donor ligand, and optionally derivatizing the resultant reaction product.

5. A process for the preparation of a compound of the formula I as claimed in claim 4, wherein $M^3$ is lithium.

6. A process for the preparation of a compound of the formula I as claimed in claim 4, wherein X is chlorine.

7. A catalyst composition which comprises: a compound of the formula I as claimed in claim 1 and an aluminoxane.

8. A compound as claimed in claim 1, wherein $M^1$ is zirconium, hafnium or titanium.

9. [a] *A* compound as claimed in [calim] *claim* 1, wherein $R^1$ and $R^2$ are identical or different and are a hydrogen atom, a $C_1$–$C_3$-alkyl group, a $C_1$–$C_3$-alkoxy group, a $C_6$–$C_8$-aryl group, a $C_6$–$C_8$-aryloxy group, a $C_2$–$C_4$-alkenyl group, a $C_7$–$C_{10}$-arylalkyl group, a $C_7$–$C_{12}$-alkylaryl group, a $C_8$–$C_{12}$-arylalkenyl group or chlorine.

10. A compound as claimed in claim 1, wherien $R^3$ and $R^4$ are identical or different and are a hydrogen atom, a fluorine, chlorine or bromine atom, a $C_1$–$C_4$-alkyl group which may be halogenated, a $C_6$–$C_8$-aryl group, a —$NR_2^{10}$, —$SR^{10}$, —$OSiR_3^{10}$, —$SiR_3^{10}$ or —$PR_2^{10}$ radical in which $R^{10}$ is a chlorine atom, or a $C_1$–$C_3$ alkyl group or a $C_6$–$C_8$-aryl group.

11. A compound as claimed in claim 1, wherein $R^3$ and $R^4$ are hydrogen.

12. A compound as claimed in claim 1, wherein $R^5$ and $R^6$ are identical.

13. A compound as claimed in claim 1, wherein $R^5$ and $R^6$ are ($C_1$–$C_4$)-alkyl, which may be halogenated with methyl.

14. A compound as claimed in claim 1, wherein $R^{11}$, $R^{12}$ and $R^{13}$ are identical or different and are a hydrogen atom, a halogen atom, a $C_1$–$C_4$-alkyl group, a $CF_3$ group, a $C_6$–$C_8$-aryl group, a pentafluorophenyl group, a $C_1$–$C_4$-alkoxy group a $C_2$–$C_4$-alkenyl group, a $C_7$–$C_{10}$-arylalkyl group, a $C_8$–$C_{12}$-arylalkenyl group and a $C_7$–$C_{12}$-alkylaryl group, or $R^{11}$ or $R_{12}$ or $R^{11}$ and $R^{13}$, in each case together with the atoms connecting them, form a ring.

15. A compound as claimed in claim 1, wherein $M^2$ is silicon or germanium.

16. A compound as claimed in claim 1, wherein $R^7$ is $=CR^{11}R^{12}$, $=SiR^{11}R^{12}$, $=GeR^{11}R^{12}$, —O—, —S—, =SO, $=PR^{11}$ or $=P(O)R^{11}$.

[17. A compound as claimed in claim 1, wherein m and n are identical or different and are zero or 1].

[18. A compound as claimed in claim 1, wherein m plus n is zero or 1].

19. A compound as claimed in claim 1, wherein $M^1$ is Zr or Hf, $R^1$ and $R^2$ are identical or different and are methyl or chlorine, $R^3$ and $R^4$ are hydrogen, $R^5$ and $R^6$ are identical or different and are methyl, ethyl or trifluoromethyl, and n plus m is zero [or 1].

*20. A compound of the formula I*

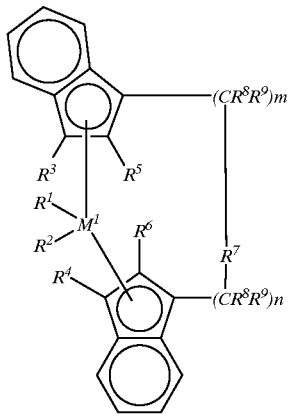

*in which*

*$M^1$ is zirconium or titanium,*

*$R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom,*

*$R^3$ and $R^4$ are identical or different and are a hydrogen atom, a halogen atom, a $C_1$–$C_{10}$-alkyl group, which is optionally halogenated, a $C_6$–$C_{10}$-aryl group, an —$NR_2^{10}$, —$SR^{10}$, —$OSiR_3^{10}$, —$SiR_3^{10}$ or —$PR_2^{10}$ radical in which $R^{10}$ is a halogen atom, a $C_1$–$C_{10}$-alkyl group or a $C_6$–$C_{10}$-aryl group,*

*$R^5$ and $R^6$ are identical or different and are as defined for $R^3$ and $R^4$, with the proviso that $R^5$ and $R^6$ are not hydrogen,*

*$R^7$ is*

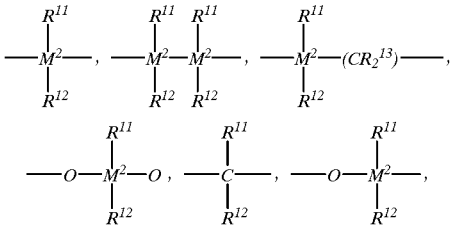

*$=BR^{11}$, $=AlR^{11}$, —Ge—, —Sn—, —O—, —S—, =SO, $=SO_2$, $=NR^{11}$, =CO, $=PR^{11}$ or $=P(O)R^{11}$, where $R^{11}$, $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{11}$ and $R^{12}$ or $R^{11}$ and $R^{13}$, in each case with the atoms connecting them, form a ring,*

*$M^2$ is silicon, germanium or tin,*

*$R^8$ and $R^9$ are identical or different and are as defined for $R^{11}$ and m and n are identical or different are zero, 1 or 2, m plus n being zero, 1 or 2.*

*21. The compound as claimed in claim 20, wherein $M^1$ is zirconium.*

*22. A compound of the formula I*

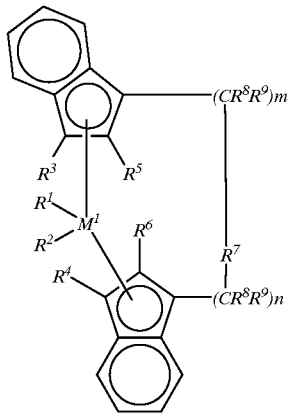

*in which*

*$M^1$ is a metal from group IVb, Vb or VIb of the Periodic Table,*

*$R^1$ is a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group,*

*$R^2$ is a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy* group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen group, $R^3$ and $R^4$ are identical or different and are a hydrogen atom, a halogen atom, a $C_1$–$C_{10}$-alkyl group, which is optionally halogenated, a $C_6$–$C_{10}$-aryl group, an $—NR_2^{10}$, $—SR^{10}$, $—OSiR_3^{10}$, $—SiR_3^{10}$ or $—PR_2^{10}$ radical in which $R^{10}$ is a halogen atom, a $C_1$–$C_{10}$-alkyl group or a $C_6$–$C_{10}$-aryl group, $R^5$ and $R^6$ are identical or different and are as defined for $R^3$ and $R^4$, with the proviso that $R^5$ and $R^6$ are not hydrogen, $R^7$ is

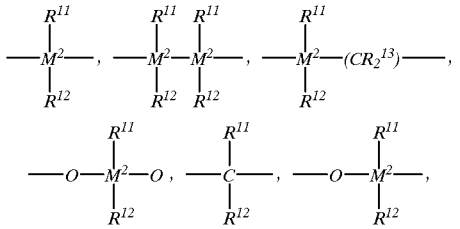

$=BR^{11}$, $=AlR^{11}$, —Ge—, —Sn—, —O—, —S—, =SO, $SO_2$, $=NR^{11}$, =CO, $=PR^{11}$ or $=P(O)R^{11}$, where $R^{11}$, and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, $R^{12}$ is a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{11}$ and $R^{12}$ or $R^{11}$ and $R^{13}$, in each case with the atoms connecting them, form a ring, $M^2$ is silicon, germanium or tin, $R^8$ and $R^9$ are identical or different and are as defined for $R^{11}$ and m and n are identical or different and are zero, 1 or 2, m plus n being zero, 1 or 2.

23. A compound of the formula I

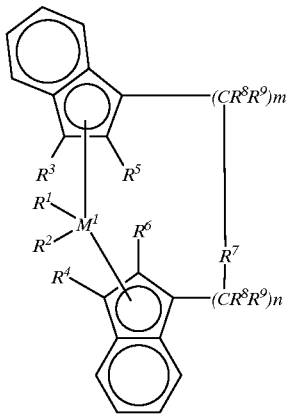

in which $M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom, $R^3$ and $R^4$ are identical or different and are a hydrogen atom, a halogen atom, a $C_1$–$C_{10}$-alkyl group, which is optionally halogenated, a $C_6$–$C_{10}$-aryl group, an $—NR_2^{10}$, $—SR^{10}$, $—OSiR_3^{10}$, $—SiR_3^{10}$ or $—PR_2^{10}$ radical in which $R^{10}$ is a halogen atom, a $C_1$–$C_{10}$-alkyl group or a $C_6$–$C_{10}$-aryl group, $R^5$ and $R^6$ are identical or different and are as defined for $R^3$ and $R^4$, with the proviso that $R^5$ and $R^6$ are not hydrogen, $R^7$ is

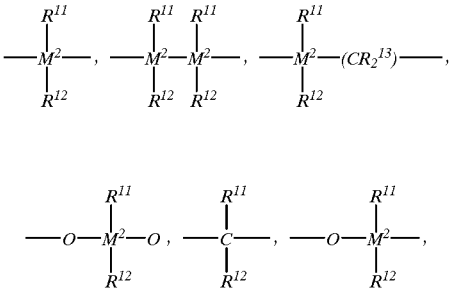

$=BR^{11}$, $=AlR^{11}$, —Ge—, —Sn—, —O—, —S—, =SO, $=SO_2$, $=NR^{11}$, =CO, $=PR^{11}$ or $=P(O)R^{11}$, where $R^{12}$ is a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, $R^{11}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{11}$ and $R^{12}$ or $R^{11}$ and $R^{13}$, in each case with the atoms connecting them, form a ring, $M^2$ is silicon, germanium or tin, $R^8$ and $R^9$ are identical or different and are as defined for $R^{11}$ and m and n are identical or different and are zero, 1 or 2, m plus n being zero, 1 or 2.

24. *A compound of the formula I*

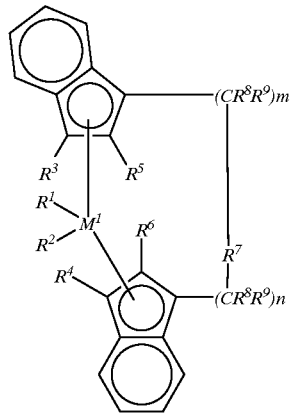

*in which*

$M^1$ *is a metal from group IVb, Vb or VIb of the Periodic Table,*

$R^1$ *and* $R^2$ *are identical or different and are a hydrogen atom, a* $C_1$–$C_{10}$*-alkyl group, a* $C_1$–$C_{10}$*-alkoxy group, a* $C_6$–$C_{10}$*-aryl group, a* $C_6$–$C_{10}$*-aryloxy group, a* $C_2$–$C_{10}$*-alkenyl group, a* $C_7$–$C_{40}$*-arylalkyl group, a* $C_7$–$C_{40}$*-alkylaryl group, a* $C_8$–$C_{40}$*-arylalkenyl group or a halogen atom,*

$R^3$ *and* $R^4$ *are identical or different and are a hydrogen atom, a halogen atom, a* $C_1$–$C_{10}$*-alkyl group, which is optionally halogenated, a* $C_6$–$C_{10}$*-aryl group, an* $—NR_2^{10}$, $—SR^{10}$, $—OSiR_3^{10}$, $—SiR_3^{10}$ *or* $—PR_2^{10}$ *radical in which* $R^{10}$ *is a halogen atom, a* $C_1$–$C_{10}$*-alkyl group or a* $C_6$–$C_{10}$*-aryl group,*

$R^5$ *and* $R^6$ *are identical or different and are as defined for* $R^3$ *and* $R^4$*, with the proviso that* $R^5$ *and* $R^6$ *are not hydrogen,*

$R^7$ *is*

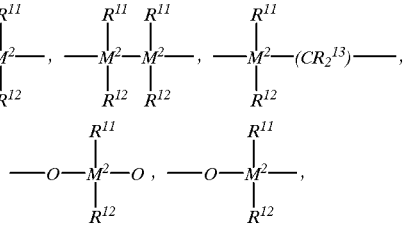

$=BR^{11}$, $=AlR^{11}$, $—Ge—$, $—Sn—$, $—O—$, $—S—$, $=SO$, $=SO_2$, $=NR^{11}$, $=CO$, $=PR^{11}$ *or* $=P(O)R^{11}$,

*where*

$R^{11}$, $R^{12}$ *and* $R^{13}$ *are identical or different and are a hydrogen atom, a halogen atom, a* $C_1$–$C_{10}$*-alkyl group, a* $C_1$–$C_{10}$*-fluoroalkyl group, a* $C_6$–$C_{10}$*-aryl group, a* $C_6$–$C_{10}$*-fluoroaryl group, a* $C_1$–$C_{10}$*-alkoxy group, a* $C_2$–$C_{10}$*-alkenyl group, a* $C_7$–$C_{40}$*-arylalkyl group, a* $C_8$–$C_{40}$*-arylalkenyl group or a* $C_7$–$C_{40}$*-alkylaryl group, or* $R^{11}$ *and* $R^{12}$ *or* $R^{11}$ *and* $R^{13}$*, in each case with the atoms connecting them, form a ring,*

$M^2$ *is germanium or tin,*

$R^8$ *and* $R^9$ *are identical or different and are as defined for* $R^{11}$ *and m and n are identical or different and are zero, 1 or 2, m plus n being zero, 1 or 2.*

25. *A compound of the formula I*

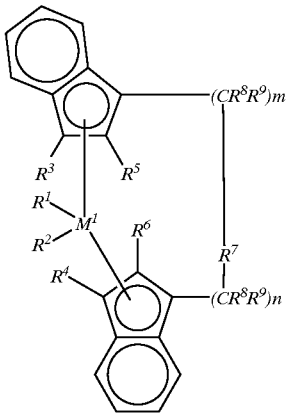

*in which*

$M^1$ *is a metal from group IVb, Vb or VIb of the Periodic Table,*

$R^1$ *and* $R^2$ *are identical or different and are a hydrogen atom, a* $C_1$–$C_{10}$*-alkyl group, a* $C_1$–$C_{10}$*-alkoxy group, a* $C_6$–$C_{10}$*-aryl group, a* $C_6$–$C_{10}$*-aryloxy group, a* $C_2$–$C_{10}$*-alkenyl group, a* $C_7$–$C_{40}$*-arylalkyl group, a* $C_7$–$C_{40}$*-alkylaryl group, a* $C_8$–$C_{40}$*-arylalkenyl group or a halogen atom,*

$R^3$ *and* $R^4$ *are identical or different and are a hydrogen atom, a halogen atom, a* $C_1$–$C_{10}$*-alkyl group which is halogenated, a* $C_6$–$C_{10}$*-aryl group, an* $—NR_2^{10}$, $—SR^{10}$, $—OSiR_3^{10}$, $—SiR_3^{10}$ *or* $—PR_2^{10}$ *radical in which* $R^{10}$ *is a halogen atom, a* $C_1$–$C_{10}$*-alkyl group or a* $C_6$–$C_{10}$*-aryl group,*

$R^5$ *and* $R^6$ *are identical or different and are a halogen atom, a* $C_1$–$C_{10}$*-alkyl group, which is optionally halogenated, a* $C_6$–$C_{10}$*-aryl group, an* $—NR_2^{10}$, $—SR^{10}$, $—OSiR_3^{10}$, $—SiR_3^{10}$ *or* $—PR_2^{10}$ *radical in which* $R^{10}$ *is a halogen atom, a* $C_1$–$C_{10}$*-alkyl group or a* $C_6$–$C_{10}$*-aryl group,*

$R^7$ *is*

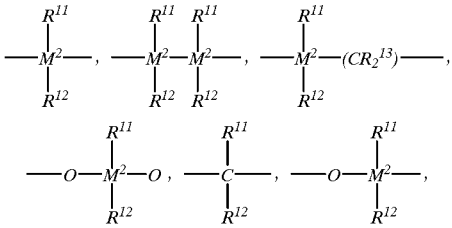

$=BR^{11}$, $=AlR^{11}$, $—Ge—$, $—Sn—$, $—O—$, $—S—$, $=SO$, $=SO_2$, $=NR^{11}$, $=CO$, $=PR^{11}$ *or* $=P(O)R^{11}$,

*where*

$R^{11}$, $R^{12}$ *and* $R^{13}$ *are identical or different and are a hydrogen atom, a halogen atom, a* $C_1$–$C_{10}$*-alkyl group, a* $C_1$–$C_{10}$*-fluoroalkyl group, a* $C_6$–$C_{10}$*-aryl group, a* $C_6$–$C_{10}$*-fluoroaryl group, a* $C_1$–$C_{10}$*-alkoxy group, a* $C_2$–$C_{10}$*-alkenyl group, a* $C_7$–$C_{40}$*-arylalkyl group, a* $C_8$–$C_{40}$*-arylalkenyl group or a* $C_7$–$C_{40}$*-alkylaryl group, or* $R^{11}$ *and* $R^{12}$ *or* $R^{11}$ *and* $R^{13}$*, in each case with the atoms connecting them, form a ring,*

$M^2$ *is silicon, germanium or tin,*

$R^8$ *and* $R^9$ *are identical or different and are as defined for* $R^{11}$ *and m and n are identical or different and are zero, 1 or 2, m plus n being zero, 1 or 2.*

26. *A compound of the formula I*

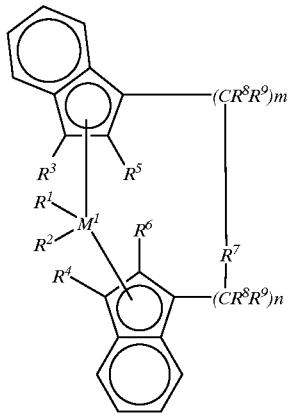

*in which*

$M^1$ *is a metal from group IVb, Vb or VIb of the Periodic Table,*

$R^1$ *and* $R^2$ *are identical or different and are a hydrogen atom, a* $C_1$–$C_{10}$*-alkyl group, a* $C_1$–$C_{10}$*-alkoxy group, a* $C_6$–$C_{10}$*-aryl group, a* $C_6$–$C_{10}$*-aryloxy group, a* $C_2$–$C_{10}$*-alkenyl group, a* $C_7$–$C_{40}$*-arylalkyl group, a* $C_7$–$C_{40}$*-alkylaryl group, a* $C_8$–$C_{40}$*-arylalkenyl group or a halogen atom,*

$R^3$ *and* $R^4$ *are identical or different and are a hydrogen atom, a halogen atom, a* $C_1$–$C_{10}$*-alkyl group, which is optionally halogenated, a* $C_6$–$C_{10}$*-aryl group, an* $—NR_2^{10}$, $—SR^{10}$, $—OSiR_3^{10}$, $—SiR_3^{10}$ *or* $—PR_2^{10}$ *radical in which* $R^{10}$ *is a halogen atom, a* $C_1$–$C_{10}$*-alkyl group or a* $C_6$–$C_{10}$*-aryl group,*

$R^5$ *and* $R^6$ *are identical or different and are a halogen atom, a* $C_1$–$C_{10}$*-alkyl group which is halogenated, a* $C_6$–$C_{10}$*-aryl group, an* $—NR—_2^{10}$, $—SR^{10}$, $—OSiR_3^{10}$, $—SiR_3^{10}$ *or* $—PR_2^{10}$ *radical in which* $R^{10}$ *is a halogen atom, a* $C_1$–$C_{10}$*-alkyl group or a* $C_6$–$C_{10}$*-aryl group,*

$R^7$ *is*

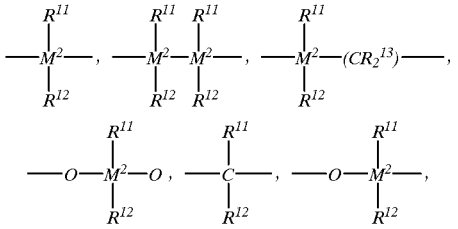

$=BR^{11}$, $=AlR^{11}$, $—Ge—$, $—Sn—$, $—O—$, $—S—$, $=SO$, $=SO_2$, $=NR^{11}$, $=CO$, $=PR^{11}$ *or* $=P(O)R^{11}$,

*where*

$R^{11}$, $R^{12}$ *and* $R^{13}$ *are identical or different and are a hydrogen atom, a halogen atom, a* $C_1$–$C_{10}$*-alkyl group, a* $C_1$–$C_{10}$*-fluoroalkyl group, a* $C_6$–$C_{10}$*-aryl group, a* $C_6$–$C_{10}$*-fluoroaryl group, a* $C_1$–$C_{10}$*-alkoxy group, a* $C_2$–$C_{10}$*-alkenyl group, a* $C_7$–$C_{40}$*-arylalkyl group, a* $C_8$–$C_{40}$*-arylalkenyl group or a* $C_7$–$C_{40}$*-alkylaryl group, or* $R^{11}$ *or* $R^{12}$ *or* $R^{11}$ *and* $R^{13}$*, in each case with the atoms connecting them, form a ring,*

$M^2$ *is silicon, germanium or tin,*

$R^8$ *and* $R^9$ *are identical or different and are as defined for* $R^{11}$ *and m and n are identical or different and are zero, 1 or 2, m plus n being zero, 1 or 2.*

27. *A compound of the formula I*

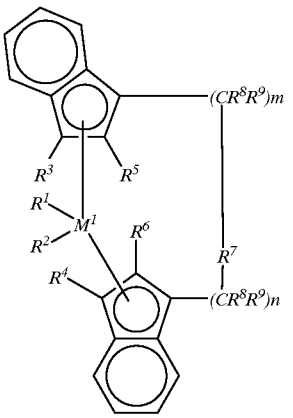

*in which*

$M^1$ *is a metal from group IVb, Vb or VIb of the Periodic Table,*

$R^1$ *and* $R^2$ *are identical or different and are a hydrogen atom, a* $C_1$–$C_{10}$*-alkyl group, a* $C_1$–$C_{10}$*-alkoxy group, a* $C_6$–$C_{10}$*-aryl group, a* $C_6$–$C_{10}$*-aryloxy group, a* $C_2$–$C_{10}$*-alkenyl group, a* $C_7$–$C_{40}$*-arylalkyl group, a* $C_7$–$C_{40}$*-alkylaryl group, a* $C_8$–$C_{40}$*-arylalkenyl group or a halogen atom,*

$R^3$ *and* $R^4$ *are different and are a hydrogen atom, a halogen atom, a* $C_1$–$C_{10}$*-alkyl group, which is optionally halogenated, a* $C_6$–$C_{10}$*-aryl group, an* $—NR_2^{10}$, $—SR^{10}$, $—OSiR_3^{10}$, $—SiR_3^{10}$ *or* $—PR_2^{10}$ *radical in which* $R^{10}$ *is a halogen atom, a* $C_1$–$C_{10}$*-alkyl group or a* $C_6$–$C_{10}$*-aryl group,*

$R^5$ *and* $R^6$ *are identical or different and are as defined for* $R^3$ *and* $R^4$*, with the proviso that* $R^5$ *and* $R^6$ *are not hydrogen,*

$R^7$ *is*

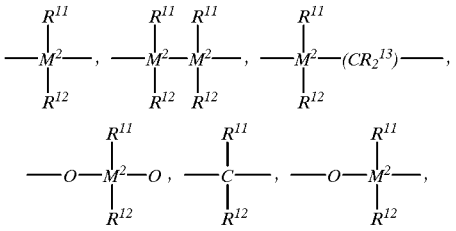

$=BR^{11}$, $=AlR^{11}$, $—Ge—$, $—Sn—$, $—O—$, $—S—$, $=SO$, $=SO_2$, $=NR^{11}$, $=CO$, $=PR^{11}$ *or* $=P(O)R^{11}$,

*where*

$R^{11}$, $R^{12}$ *and* $R^{13}$ *are identical or different and are a hydrogen atom, a halogen atom, a* $C_1$–$C_{10}$*-alkyl group, a* $C_1$–$C_{10}$*-fluoroalkyl group, a* $C_6$–$C_{10}$*-aryl group, a* $C_6$–$C_{10}$*-fluoroaryl group, a* $C_1$–$C_{10}$*-alkoxy group, a* $C_2$–$C_{10}$*-alkenyl group, a* $C_7$–$C_{40}$*-arylalkyl group, a* $C_8$–$C_{40}$*-arylalkenyl group or a* $C_7$–$C_{40}$*-alkylaryl group, or* $R^{11}$ *and* $R^{12}$ *or* $R^{11}$ *and* $R^{13}$*, in each case with the atoms connecting them, form a ring,*

$M^2$ *is silicon, germanium or tin,*

$R^8$ *and* $R^9$ *are identical or different and are as defined for* $R^{11}$ *and m and n are identical or different and are zero, 1 or 2, m plus n being zero, 1 or 2.*

* * * * *

UNITED STATES PATENT AND TRADEMARK OFFICE

CERTIFICATE OF CORRECTION

PATENT NO. : RE 37,384 E
DATED : September 18, 2001
INVENTOR(S) : Winter et al.

It is certified that error appears in the above-identified patent and that said Letters Patent is hereby corrected as shown below:

Title page,
Item [56], References Cited, U.S. PATENT DOCUMENTS "4,985,576 * 1/1991 Roarmann et al. …..… 556/11" should read -- 4,985,576 * 1/1991 Rohrmann et al. …… 556/11 --.
Item [56], References Cited, FOREIGN PATENT DOCUMENTS "0185918 * 6/1989 (EP.)" should read -- 0185918 * 9/1989 (EP.) --.

Column 15,
Line 34, ", $-OSiR_2^{10}$." should read as -- , $-OSiR_3^{10}$, --.

Column 17,
Line 25, "group, or $R^{11}$ or $R_{12}$ or …." should read as -- group, or $R^{11}$ or $R^{12}$ or …. --.

Column 18,
Line 34, "...or different are zero, 1 or" should read as -- ...or different and are zero, 1 or --.

Column 23,
Line 62, "group, or $R^{11}$ or $R^{12}$ or…" should reads as -- group, or $R^{11}$ and $R^{12}$ or… --.

Signed and Sealed this

Fourth Day of June, 2002

*Attest:*

*Attesting Officer*

JAMES E. ROGAN
*Director of the United States Patent and Trademark Office*